(12) United States Patent
Masuda et al.

(10) Patent No.: US 10,488,262 B2
(45) Date of Patent: Nov. 26, 2019

(54) INTEGRATED CIRCUIT AND MEASURING DEVICE

(71) Applicant: Sharp Kabushiki Kaisha, Sakai, Osaka (JP)

(72) Inventors: Ryohichi Masuda, Sakai (JP); Hidenori Kawanishi, Sakai (JP)

(73) Assignee: SHARP KABUSHIKI KAISHA, Sakai (JP)

( * ) Notice: Subject to any disclaimer, the term of this patent is extended or adjusted under 35 U.S.C. 154(b) by 0 days.

(21) Appl. No.: 15/567,382

(22) PCT Filed: Apr. 5, 2016

(86) PCT No.: PCT/JP2016/061160
§ 371 (c)(1),
(2) Date: Oct. 18, 2017

(87) PCT Pub. No.: WO2016/170973
PCT Pub. Date: Oct. 27, 2016

(65) Prior Publication Data
US 2018/0113029 A1 Apr. 26, 2018

(30) Foreign Application Priority Data
Apr. 20, 2015 (JP) .................. 2015-086027

(51) Int. Cl.
*G01J 5/08* (2006.01)
*A61B 5/01* (2006.01)
*G01J 5/00* (2006.01)

(52) U.S. Cl.
CPC ............ *G01J 5/0846* (2013.01); *A61B 5/01* (2013.01); *G01J 5/0809* (2013.01); *G01J 2005/0077* (2013.01)

(58) Field of Classification Search
CPC ............ G01J 5/0846; G01J 5/0809; G01J 2005/0077; G01J 2005/202; G01J 1/4228;
(Continued)

(56) References Cited

U.S. PATENT DOCUMENTS 2,199,082 A * 4/1940 Peters ................ G01J 5/08
136/215
5,565,683 A * 10/1996 Ando ................ G01S 3/784
250/338.3
(Continued)

FOREIGN PATENT DOCUMENTS

JP 2003241064 A * 8/2003
JP 2006-174919 A 7/2006
(Continued)

OTHER PUBLICATIONS

AIPN English translation of Nippon Co. JP 2014-135993.*
(Continued)

*Primary Examiner* — Mohamed K Amara
(74) *Attorney, Agent, or Firm* — Keating & Bennett, LLP

(57) ABSTRACT

An integrated circuit includes a first detection element that detects a temperature of an object based on infrared light reflected from the object and a second detection element that detects an image of the object based on visible light reflected from the object on the same substrate.

10 Claims, 12 Drawing Sheets

(58) Field of Classification Search
CPC .............. G01J 2003/2826; A61B 5/01; A61B
2560/0242; A61B 2560/0431; A61B
5/0022; A61B 2018/00714; A61B
2018/00791; A61B 2018/2065; A61B
2018/207; A61B 5/02433; G05D 1/0274;
G05D 1/0227; G05D 1/0242; G05D
1/0246; G05D 1/0251; B25J 19/023;
Y10S 901/01; Y10S 901/47; G06F
19/3418; G02B 2027/0138; G02B
27/0172; G02B 5/201; G02B 26/101;
G02B 26/105; G06K 9/2018; B60S
1/0844
See application file for complete search history.

(56) References Cited

U.S. PATENT DOCUMENTS

| | | | | |
|---|---|---|---|---|
| 8,670,892 | B2 * | 3/2014 | Yang | G05D 1/0242 187/222 |
| 9,610,042 | B1 * | 4/2017 | Vyshedskiy | A61B 5/6898 |
| 2007/0284532 | A1 * | 12/2007 | Nakanishi | G01J 3/36 250/339.02 |
| 2008/0259187 | A1 * | 10/2008 | Izawa | G06K 9/2018 348/241 |
| 2009/0015388 | A1 * | 1/2009 | Yagi | B60Q 1/0035 340/435 |
| 2009/0032678 | A1 * | 2/2009 | Taniguchi | G03B 17/00 250/201.2 |
| 2009/0253144 | A1 * | 10/2009 | Venkitaraman | G01N 33/5017 435/6.16 |
| 2014/0098236 | A1 * | 4/2014 | Holliday | G01J 5/026 348/164 |
| 2015/0009335 | A1 * | 1/2015 | Strandemar | H04N 5/33 348/164 |
| 2016/0070339 | A1 * | 3/2016 | Crawford | A61B 5/01 345/156 |
| 2016/0154151 | A1 * | 6/2016 | Cha | G02B 5/201 348/342 |
| 2016/0210747 | A1 * | 7/2016 | Hay | G06T 7/11 |
| 2016/0213325 | A1 | 7/2016 | Sogo et al. | |
| 2016/0255286 | A1 * | 9/2016 | Tsukada | H04N 5/332 348/162 |
| 2018/0088583 | A1 * | 3/2018 | Wang | B25J 11/009 |

FOREIGN PATENT DOCUMENTS

JP   2014-135993 A   7/2014
JP   5640265 B1   12/2014

OTHER PUBLICATIONS

Espacenet English Translation of Satoshi (2003)—JP 2003-241064.*
Official Communication issued in International Patent Application No. PCT/JP2016/061160, dated Jun. 21, 2016.

* cited by examiner

| COLOR | REFLECTANCE (%) | | |
|---|---|---|---|
| | BRIGHT | AVERAGE | DARK |
| YELLOW | 70 | 50 | 30 |
| BEIGE | 65 | 45 | 25 |
| ⋮ | ⋮ | ⋮ | ⋮ |
| BLACK | — | 4 | — |

FIG. 10

| SAMPLE | TIME | | |
| --- | --- | --- | --- |
| | 10:00 | 10:10 | ... |
| NO. | BODY TEMPERATURE (°C) | | |
| 1 | 36.5 | 36.5 | ... |
| 2 | 36.3 | 36.0 | ... |
| 3 | 36.7 | 37.5 | ... |
| ... | ... | ... | ... |

FIG. 11

| TIME | BODY TEMPERATURE (°C) | | | | | | INCREASE RATE (%) |
| --- | --- | --- | --- | --- | --- | --- | --- |
| | 35-36 | 36-37 | 37-38 | 38-39 | 39-40 | 38 OR HIGHER | |
| 10:00 | 0 | 93 | 7 | 0 | 0 | 0 | 0 |
| 10:10 | 0 | 91 | 9 | 0 | 0 | 0 | 0 |
| 10:20 | 0 | 94 | 5 | 1 | 0 | 1 | 1 |
| 10:30 | 0 | 29 | 28 | 39 | 4 | 43 | 42 |
| 10:40 | 0 | 0 | 35 | 39 | 22 | 62 | 19 |
| 10:50 | 0 | 0 | 0 | 39 | 53 | 92 | 30 |
| 11:00 | 0 | 0 | 0 | 42 | 53 | 95 | 3 |
| ... | ... | ... | ... | ... | ... | ... | ... |

INTEGRATED CIRCUIT AND MEASURING DEVICE

TECHNICAL FIELD

The present invention relates to an integrated circuit and a measuring device.

The present disclosure contains subject matter related to that disclosed in Japanese Priority Patent Application JP 2015-086027 filed in the Japan Patent Office on Apr. 20, 2015, the entire contents of which are hereby incorporated by reference.

BACKGROUND ART

In recent years, movements to accumulate a large amount of data represented by big data to be used for detecting, predicting, grasping, and the like of an event are becoming active. With the technological development of large-scale databases and search systems capable of processing a large amount of data, the possibility of using big data as future management and new business has been shown.

Here, big data is a term that represents a collection of huge and complicated data sets that is difficult to process with commercially available database management tools or known data processing applications. For example, concerning prevention of disease, there is a concern that expansion of disease on a global scale in a short period is accompanied by recent globalization and borderless countries. Against such a background, for example, in order to prevent infection and expansion of diseases such as influenza, there is a growing need for instruments that instantly measure and monitor the temperature of a monitored person in public places, public institutions, companies, and the like where many people gather.

For example, PTL 1 describes a technique that performs a body temperature analysis based on a thermal image from an infrared camera that images a plurality of persons existing in a spatial area and notifies information on a body temperature abnormality.

CITATION LIST

Patent Literature

PTL 1: Japanese Unexamined Patent Application Publication No. 2006-174919

SUMMARY OF INVENTION

Technical Problem

However, in the technique as described in PTL 1, since a thermal image is used, it is difficult to analyze the characteristics of a person with a fever. That is, with the technique described in PTL 1, it is difficult to analyze the characteristics of an object along with the temperature of the object (object to be measured).

One aspect of the present invention is to solve the above problem, and the purpose thereof is to provide an integrated circuit and a measuring device which makes it possible to analyze the characteristics of the object along with the temperature of the object.

Solution to Problem

In order to solve the above problem, an aspect of the present invention is to provide an integrated circuit including, on a same substrate, a first detection element that detects a temperature of an object based on infrared light reflected from the object and a second detection element that detects an image of the object based on visible light reflected from the object.

In addition, in the integrated circuit described above according to the aspect of the present invention, the first detection element detects the temperature of the object based on the infrared light and reflectance of the object generated based on the image detected by the second detection element.

Furthermore, in the integrated circuit above according to the aspect of the present invention, the reflectance of the object is generated based on a color and a brightness of the object based on the image detected by the second detection element.

In addition, the integrated circuit above according to the aspect of the present invention further includes a plurality of second detection elements disposed around the first detection element so that distances from the first detection element are equal to each other and a correction unit that generates corrected images at measurement positions of the first detection element based on images detected by the plurality of second detection elements and outputs the generated corrected images as images of the object.

Furthermore, another aspect of the present invention is to provide a measuring device including the integrated circuit, an optical path changing unit that is capable of changing optical paths of infrared light and visible light incident from each of division areas into which a predetermined detection range is divided and emitting the infrared light and the visible light toward the first detection element and the second detection element, and a measurement control unit that causes the optical path changing unit to emit, to the integrated circuit, the infrared light and the visible light incident from each of the division areas into which the predetermined detection range is divided while changing the division areas and causes the integrated circuit to detect a temperature and an image for each of the division areas.

In addition, the measuring device above according to the aspect of the present invention further includes an output processing unit that generates images of the predetermined detection range based on the image of the object and the temperature of the object in each of the division areas detected by the integrated circuit and outputs the images of the predetermined detection range and the temperature of the object in each of the division areas in association with each other.

Advantageous Effects of Invention

According to the aspects of the present invention, it is possible to analyze the characteristics of the object along with the temperature of the object.

BRIEF DESCRIPTION OF DRAWINGS

FIG. 10 is a first diagram showing an example of an analysis result of the monitoring system according to the third embodiment.

FIG. 11 is a second diagram showing an example of the analysis result of the monitoring system according to the third embodiment.

DESCRIPTION OF EMBODIMENTS

Figure 1:
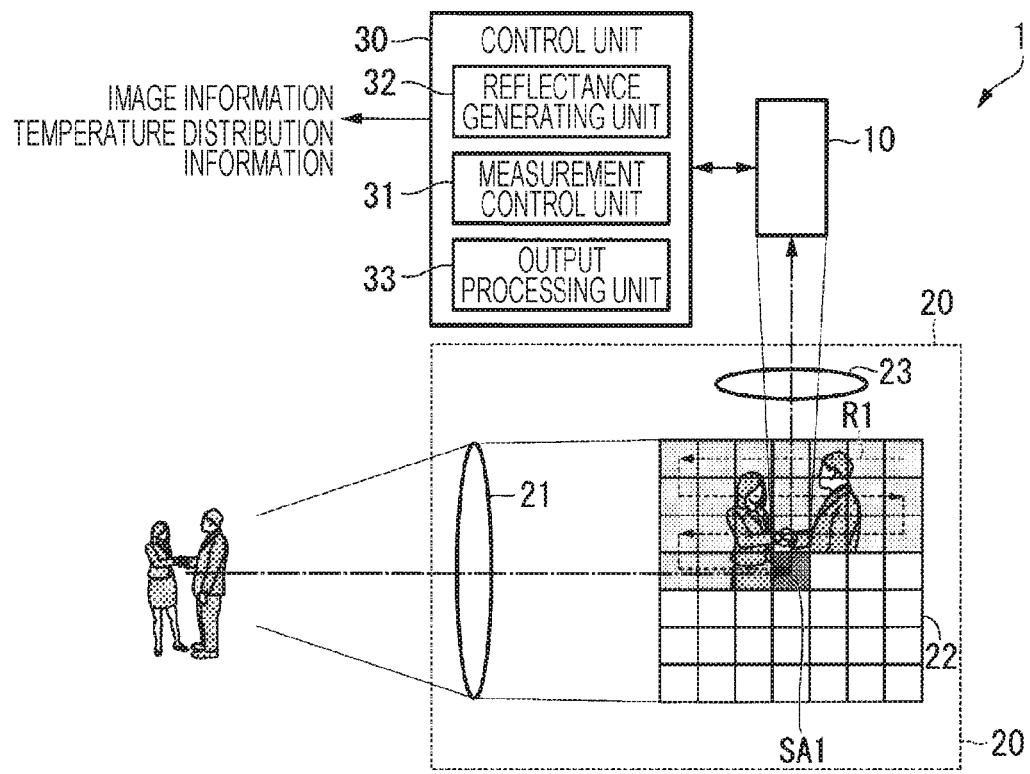
FIG. 1 is a diagram showing a configuration example of a measuring device according to a first embodiment.

Hereinafter, a measuring device and a monitoring system according to one embodiment of the present invention will be described with reference to the drawing.

First Embodiment

FIG. 1 is a diagram showing a configuration example of a measuring device 1 according to a first embodiment.

As shown in FIG. 1, the measuring device 1 includes a sensor unit 10, an optical system 20, and a control unit 30.

The sensor unit 10 (an example of the integrated circuit) is, for example, a semiconductor device that detects the temperature of an object (object to be measured) in a non-contact manner. Based on the infrared light reflected from the object, the sensor unit 10 detects the temperature of the object and detects an image of the object based on the visible light reflected from the object. The sensor unit 10 includes, for example, a thermopile unit 11 and a photodiode unit 12 as shown in FIG. 2.

Figure 2:
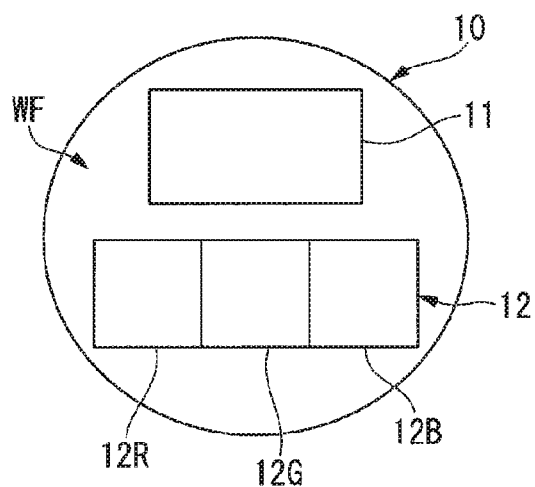
FIG. 2 is a diagram showing a configuration example of an incident surface of light of a sensor unit according to the first embodiment.

FIG. 2 is a diagram showing a configuration example of an incident surface of light of the sensor unit 10 according to the present embodiment. Here, this diagram shows the sensor unit 10 as seen from an incident surface (sensor surface) side.

As shown in FIG. 2, the sensor unit 10 includes the thermopile unit 11 and the photodiode unit 12 on the same semiconductor substrate WF. That is, in the sensor unit 10, the thermopile unit 11 and the photodiode unit 12 are formed on the semiconductor substrate WF.

The thermopile unit 11 (an example of the first detection element) detects the temperature of the object based on the infrared light reflected from the object. The thermopile unit 11 detects the temperature based on the infrared light using a thermopile 111 (see FIG. 4) to be described later.

The photodiode unit 12 (an example of the second detection element) detects an image (color information) of the object based on the visible light reflected from the object. The photodiode unit 12 includes a red photodiode unit 12R, a green photodiode unit 12G, and a blue photodiode unit 12B, and detects the intensities of the light of the three primary colors of red, green, and blue and outputs an image (color information of RGB).

Here, the red photodiode unit 12R includes a red filter (not shown) and detects the intensity of the red light in the visible light. In addition, the green photodiode unit 12G includes a green filter (not shown) and detects the intensity of the green light in the visible light. In addition, the blue photodiode unit 12B includes a blue filter (not shown) and detects the intensity of the blue light in the visible light.

Details of the configuration of the sensor unit 10 will be described later with reference to FIG. 4.

Returning to the description of FIG. 1, an optical system 20 directs the reflected light including the infrared light and the visible light from the object to the incident surface (sensor surface) of the sensor unit 10. The optical system 20 includes an optical path changing unit that changes an optical path of the reflected light incident from respective division areas where a range (predetermined detection range) of a temperature detection target is divided into a plurality of division areas (for example, pixel areas) and is capable of emitting the light toward the incident surface (sensor surface) of the sensor unit 10. The optical system 20 includes, for example, lenses (21 and 23) and a digital mirror device 22. In the present embodiment, an example in which the optical system 20 includes the digital mirror device 22 as an example of the optical path changing unit will be described.

The lens 21 is a condensing lens that focuses the reflected light including the infrared light and the visible light from the object onto the digital mirror device 22. The lens 21 is disposed between the object and the digital mirror device 22 and emits the incident reflected light to the digital mirror device 22.

The digital micromirror device (DMD) 22 (an example of the optical path changing unit) is a micro electro mechanical systems (MEMS) mirror, which changes the optical path of the reflected light incident from the lens 21 and emits the light toward the incident surface (sensor surface) of the sensor unit 10. The digital mirror device 22 changes the optical path of the infrared light and the visible light incident from, for example, respective division areas (for example, pixel areas) where the range of the temperature detection target is divided into a plurality of division areas (for example, pixel areas). The digital mirror device 22 emits the infrared light and the visible light whose optical path has been changed toward the incident surface (sensor surface) of the above-described sensor unit 10.

The digital mirror device 22 is controlled by the control unit 30 (a measurement control unit 31 to be described later) and causes the sensor unit 10 to detect the image and temperature of the target range by sequentially changing the optical path of the reflected light from respective division areas within the range of the temperature detection target and emitting the light toward the incident surface (sensor surface) of the sensor unit 10. The example shown in FIG. 1 shows a state in which the digital mirror device 22 changes division areas to be sequentially detected according to a route R1 under the control of the control unit 30 (the measurement control unit 31 to be described later) and the reflected light in a division area SA1 is emitted toward the incident surface (sensor surface) of the sensor unit 10 as a current detection area.

The lens 23 is a projection lens that projects the reflected light including the infrared light and the visible light from the digital mirror device 22 onto the incident surface (sensor surface) of the sensor unit 10. The lens 23 is disposed between the digital mirror device 22 and the sensor unit 10 and emits the incident reflected light to the sensor unit 10.

The control unit 30 is, for example, a processor including a central processing unit (CPU) or the like and controls the measuring device 1 in an integrated manner. The control unit 30 controls, for example, the sensor unit 10 and the digital mirror device 22 and controls to acquire the temperature and image (temperature and color information (pixel information) of the above-described division areas)) detected by the sensor unit 10. Then, based on the acquired temperature and image, the control unit 30 generates a temperature distribution of the range of the temperature detection target and image information of the target range and performs control for outputting the generated image information and the temperature distribution in association with each other to the outside.

In addition, the control unit 30 includes the measurement control unit 31, a reflectance generating unit 32, and an output processing unit 33.

The measurement control unit 31 controls the digital mirror device 22 to acquire a temperature and an image from the sensor unit 10. That is, the measurement control unit 31 causes the digital mirror device 22 to emit, to the sensor unit 10, the infrared light and the visible light incident from each of division areas, into which the predetermined detection range is divided, while changing the division areas. Then, the measurement control unit 31 causes the sensor unit 10 to detect a temperature and an image (color information of RGB) for each of the division areas. The measurement control unit 31 acquires the temperature and the image (color information of RGB) for each division area detected by the sensor unit 10.

The reflectance generating unit 32 generates the reflectance of the object based on the image (color information of RGB) acquired from the sensor unit 10. Here, the thermopile unit 11 of the sensor unit 10 detects the temperature using the thermopile 111, but for this detection, it is necessary to specify the reflectance of the object. The reflectance varies depending on a material, and in a case where a measurement target is not limited, it is necessary to measure the reflectance of the object for each measurement and perform reflectance correction. Therefore, the reflectance generating unit 32 limits the material of the object to "human skin" and "clothing" by limiting the material to a purpose of measuring the temperature of a person in a crowd and generate reflectance based on colors and brightness.

The reflectance generating unit 32 generates, for example, colors and brightness of the division area based on the image (color information of RGB) in the division area acquired by the measurement control unit 31 from the sensor unit 10. Here, the reflectance generating unit 32 determines colors such as "yellow", "beige", and the like based on the color information of RGB. In addition, based on the color information of RGB, the reflectance generating unit 32 determines the brightness in three stages of "bright", "average", and "dark". Based on the determined color and brightness of the division area, the reflectance generating unit 32 generates reflectance of the division area using a conversion table as shown in FIG. 3, for example.

Figures 3, 4:
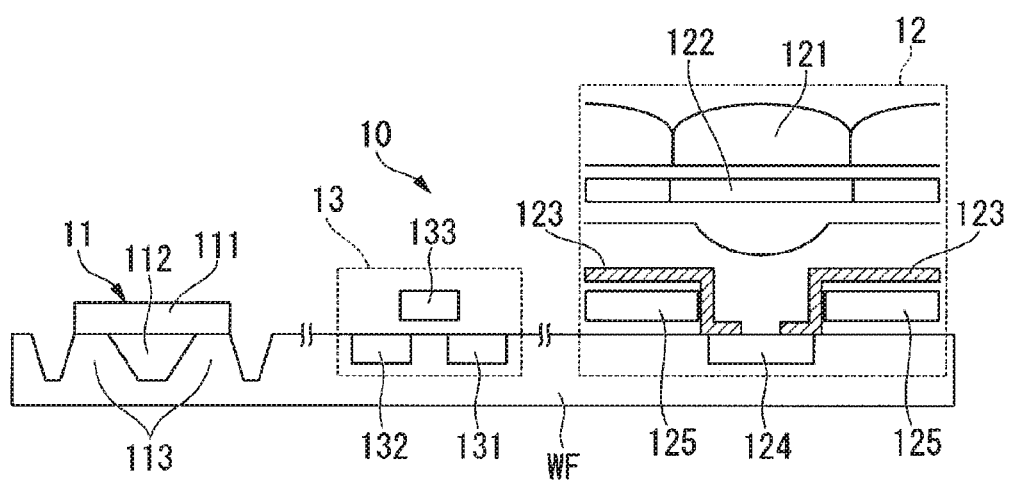
FIG. 3 is a diagram showing an example of a conversion table of reflectance.
FIG. 4 is a cross-sectional view showing an example of a cross-sectional structure of the sensor unit according to the first embodiment.

FIG. 3 is a diagram showing an example of the conversion table of reflectance.

The conversion table shown in this diagram is a table that generates the reflectance of a color diffusion plane based on a color and brightness. In this conversion table, "color" and "reflectance (%)" are associated with each other, and "reflectance (%)" is classified into three stages of "bright", "average", and "dark".

For example, in a case where "color" is "yellow" and brightness is "bright", the reflectance generating unit 32 generates "70" as "reflectance (%)" based on the conversion table. The reflectance generating unit 32 outputs the generated reflectance (in this case, "70" (%)) to the sensor unit 10.

In this way, the sensor unit 10 can accurately detect the temperature of the object based on the reflectance for each division area generated by the reflectance generating unit 32.

In this way, the thermopile unit 11 detects the temperature of the object based on the infrared light and the reflectance of the object generated based on the image detected by the photodiode unit 12.

The output processing unit 33 generates an image of the predetermined detection range based on the image of the object and the temperature of the object in each division area detected by the sensor unit 10 and outputs the image of the predetermined detection range in association with the temperature of the object in each division area. The output processing unit 33 generates image information in the range of the temperature detection target based on the image in the division area acquired by the measurement control unit 31 (color information of RGB), for example. In addition, the output processing unit 33 generates a temperature distribution of the range of the temperature detection target, for example, based on the temperature in the object of the division area obtained by the measurement control unit 31. The output processing unit 33 outputs the generated image information and the temperature distribution in association with each other to the outside.

Next, the configuration of the sensor unit 10 will be described with reference to FIG. 4.

FIG. 4 is a cross-sectional diagram showing an example of a sectional structure of the sensor unit 10 according to the present embodiment.

In the example shown in FIG. 4, the thermopile unit 11 and the photodiode unit 12 are formed on the same semiconductor substrate WF.

The thermopile unit 11 has the thermopile 111 formed so as to straddle a cavity 112 and contact a heat sink portion 113. The thermopile 111 is formed by connecting a plurality of thermocouples in series or in parallel in which two kinds of metals (not shown) or semiconductors (not shown) are bonded so as to straddle a heat insulating thin film (not shown) formed on the upper surface of the cavity 112 and the heat sink portion 113. Here, in the plurality of thermocouples, a cold junction is formed on the heat sink portion 113, and a hot junction is formed on the heat insulating thin film. The thermopile 111 outputs a voltage proportional to a local temperature difference or temperature gradient.

The photodiode unit 12 includes a microlens 121, a color filter 122, a light shielding film 123, a photodiode 124, and a polysilicon 125. In the explanation of this diagram, for example, the red photodiode unit 12R is described, but the configuration of the green photodiode unit 12G and the blue photodiode unit 12B is the same except that the color of the color filter 122 is different. Although not shown, the photodiode unit 12 includes three kinds of photodiodes, the red photodiode unit 12R, the green photodiode unit 12G, and the blue photodiode unit 12B.

The microlens 121 is a lens for guiding visible light to the photodiode 124 and emits red light to the photodiode 124 via the color filter 122 (in this case, a red filter).

The light shielding film 123 is formed in a range including the upper part of the polysilicon 125 and shields light other than the photodiode 124 so as not to be irradiated with light.

The photodiode 124 converts the irradiated light into a voltage corresponding to the intensity.

The polysilicon 125 is used to control the photodiode 124 such as outputting a voltage from the photodiode 124, initializing the state of the photodiode 124, and so on.

In addition, the sensor unit 10 includes, for example, a transistor 13 on the same semiconductor substrate WF. The transistor 13 is a MOS transistor (Metal-Oxide-Semiconductor field-effect transistor) including a source portion 131, a drain portion 132, and a gate portion 133 of the polysilicon. For example, the transistor 13 is a switching element which is necessary in the case of performing control such as transferring the signal of the thermopile unit 11 or the photodiode unit 12 to the control unit 30.

Next, the operation of the measuring device 1 according to the present embodiment will be described with reference to FIG. 5.

Figure 5:
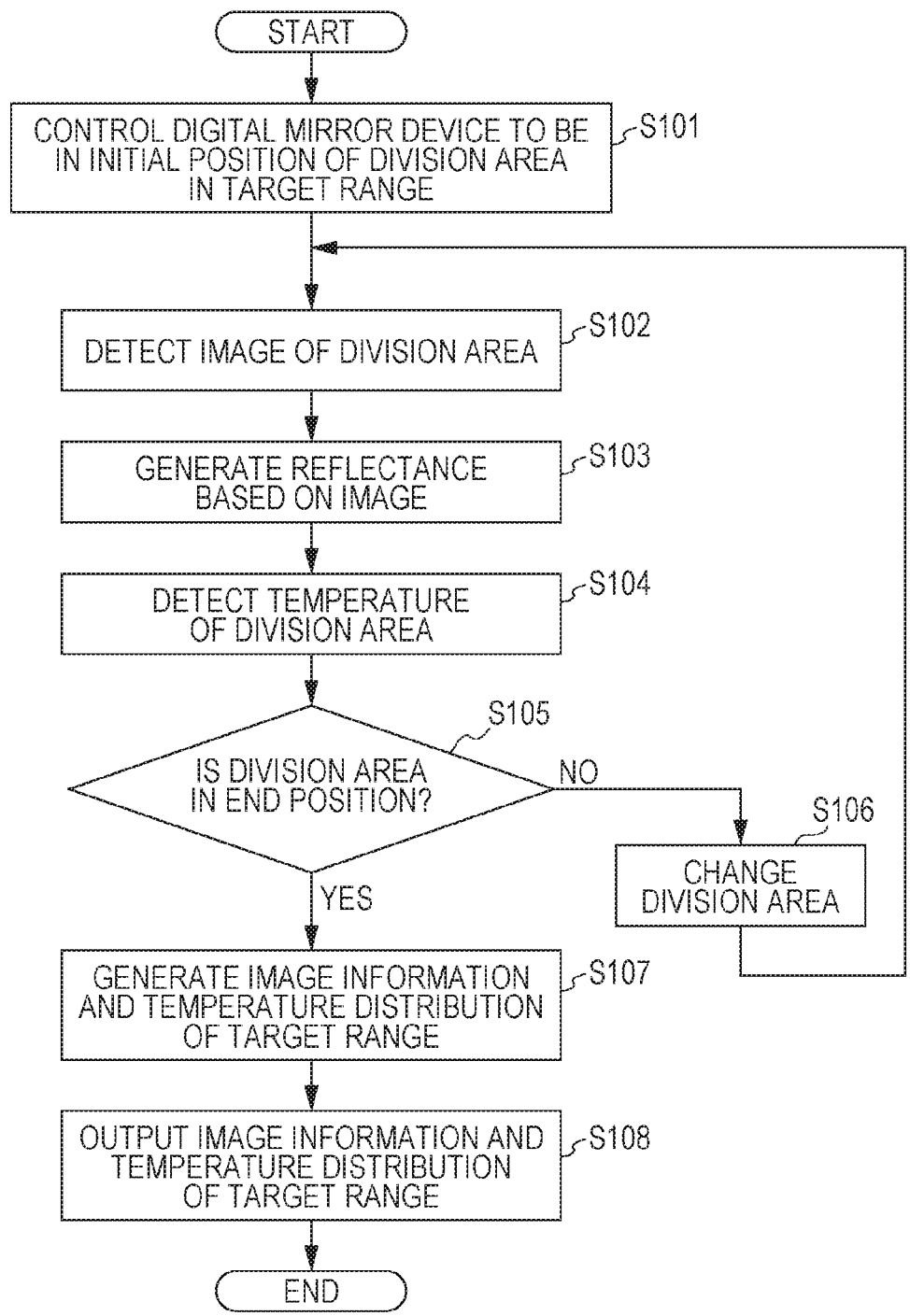
FIG. 5 is a flowchart showing an example of an operation of the measuring device according to the first embodiment.

FIG. 5 is a flowchart showing an example of the operation of the measuring device 1 according to the present embodiment.

As shown in FIG. 5, the measuring device 1 first controls the digital mirror device 22 to be in an initial position of the division area in the target range (step S101). That is, the measurement control unit 31 of the control unit 30 controls the digital mirror device 22 so that the reflected light of the initial position of the division area in the range of the temperature detection target is emitted to the sensor unit 10.

Next, the measurement control unit 31 detects the image of the division area (step S102). That is, the measurement control unit 31 causes the sensor unit 10 to detect the image of the division area (color information of RGB) and obtains the image (color information of RGB) of the division area detected by the photodiode unit 12 of the sensor unit 10.

Next, the reflectance generating unit 32 of the control unit 30 generates reflectance based on the image (step S103). The reflectance generating unit 32 generates, for example, colors and brightness of the division area based on the image (color information of RGB) in the division area acquired by the measurement control unit 31 from the sensor unit 10. Based on the generated color and brightness of the division area, the reflectance generating unit 32 generates reflectance of the division area using a conversion table as shown in FIG. 3, for example. Then, the reflectance generating unit 32 outputs the generated reflectance of the division area to the sensor unit 10.

Next, the measurement control unit 31 detects the temperature of the division area (step S104). That is, the measurement control unit 31 causes the sensor unit 10 to detect the temperature of the division area and acquires the temperature of the division area detected by the thermopile unit 11 of the sensor unit 10. The reflectance generated by the reflectance generating unit 32 is used when the thermopile unit 11 detects the temperature of the object based on infrared light.

Next, the measurement control unit 31 determines whether or not the division area is in an end position (step S105). The measurement control unit 31 determines whether or not the division area is in the end position in the range of the temperature detection target. In a case where the division area is in the end position (step S105: YES), the measurement control unit 31 advances the processing to step S107. In addition, in a case where the division area is not in the end position (step S105: NO), the measurement control unit 31 advances the processing to step S106.

In step S106, the measurement control unit 31 changes the division area, returns the processing to step S102, and repeats the processing from step S102 to step S105 until the division area reaches the end position.

In addition, in step S107, the output processing unit 33 of the control unit 30 generates image information and a temperature distribution of the target range. The output processing unit 33 generates image information and a temperature distribution of the target range based on the image of the object in respective division areas detected by the sensor unit 10 and the temperature of the object.

Next, the output processing unit 33 outputs the image information and the temperature distribution of the target range (step S108).

As described above, the sensor unit 10 (an example of the integrated circuit) according to the present embodiment includes the thermopile unit 11 (the first detection element) and the photodiode unit 12 (the second detection element) on the same substrate (for example, on the semiconductor substrate WF). The thermopile unit 11 detects the temperature of the object based on the infrared light reflected from the object. The photodiode unit 12 detects the image of the object based on the visible light reflected from the object.

In this way, because the sensor unit 10 according to the present embodiment may detect the image of the object along with the temperature of the object, it is possible to analyze the characteristics of the object along with the temperature of the object.

In addition, in the present embodiment, the thermopile unit 11 detects the temperature of the object based on the infrared light and the reflectance of the object generated based on the image detected by the photodiode unit 12.

In this way, the sensor unit 10 according to the present embodiment may detect the temperature more accurately by the reflectance generated based on the image.

In addition, in the present embodiment, the reflectance of the object is generated based on the colors and brightness of the object on the basis of the image detected by the photodiode unit 12. For example, the reflectance generating unit 32 generates reflectance based on colors and brightness, for example, using the conversion table as shown in FIG. 3.

In this way, the sensor unit 10 according to the present embodiment may detect the temperature more accurately by the reflectance generated by a simple method. In addition, the measuring device 1 according to the present embodiment may detect the temperature more accurately by generating appropriate reflectance by the simple method.

In addition, the measuring device 1 according to the present embodiment, includes the above-described sensor unit 10, an optical path changing unit (for example, the digital mirror device 22), and the measurement control unit 31. The digital mirror device 22 is an optical path changing unit that changes the optical path of infrared light and visible light incident from respective division areas into which the predetermined detection range is divided into a plurality of division areas so that the infrared light and visible light can be emitted to the thermopile unit 11 and the photodiode unit 12. Then, the measurement control unit 31 causes the digital mirror device 22 to emit, to the sensor unit 10, the infrared light and visible light incident from each of division areas, into which the predetermined detection range is divided, while changing the division areas, and causes the sensor unit 10 to detect the temperature and image for each of the division areas.

In the thermopile unit 11 of the sensor unit 10, the wider the area of a light receiving portion (thermopile 111), the higher the detection accuracy of a temperature. For that reason, by changing the optical path by the optical path changing unit (for example, the digital mirror device 22), the measuring device 1 may widen the area of the light receiving portion (thermopile 111), for example, compared to a case where a plurality of the thermopile units 11 (thermopile 111) are disposed in a matrix. Therefore, the measuring device 1 according to the present embodiment may improve the accuracy of detecting the temperature.

In addition, in the present embodiment, the above-described optical path changing unit includes the digital mirror device 22.

In this way, the measuring device 1 according to the present embodiment may improve the accuracy of temperature detection by a simple method using the digital mirror device 22.

Second Embodiment

Next, the operation of the measuring device according to the second embodiment will be described with reference to the drawing.

Figure 6:
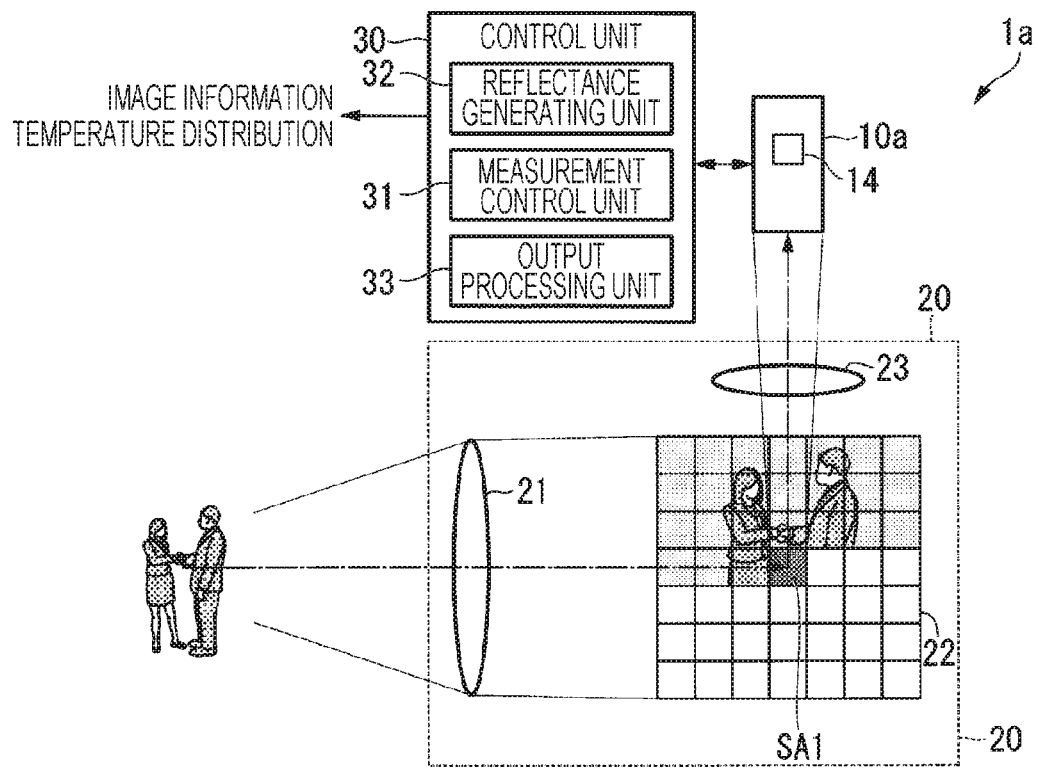
FIG. 6 is a diagram showing a configuration example of a measuring device according to a second embodiment.

FIG. 6 is a diagram showing a configuration example of a measuring device 1*a* according to a second embodiment. In addition, FIG. 7 is a diagram showing a configuration example of an incident surface of light of a sensor unit 10*a* according to the second embodiment.

Figure 7:
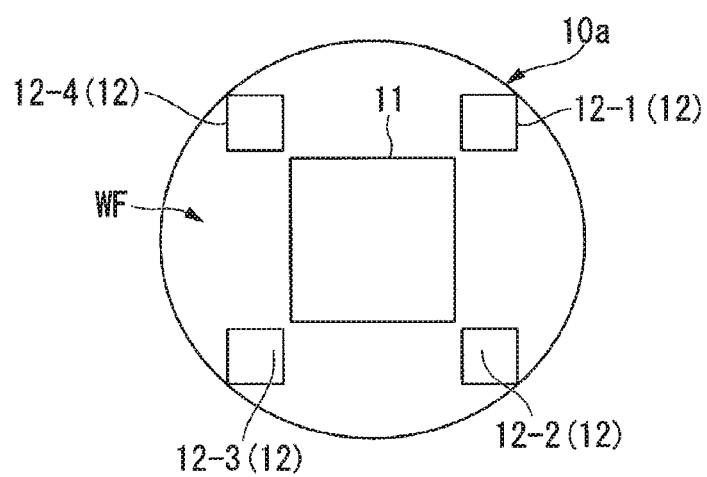
FIG. 7 is a diagram showing a configuration example of an incident surface of light of a sensor unit according to the second embodiment.

In FIGS. 6 and 7, the same components as those shown in FIGS. 1 and 2 are denoted by the same reference numerals, and the description thereof will be omitted.

As shown in FIG. 6, the measuring device 1*a* according to the present embodiment includes a sensor unit 10*a*, the optical system 20, and the control unit 30. In addition, the sensor unit 10*a* includes an image correction unit 14.

In addition, as shown in FIG. 7, the sensor unit 10*a* includes the thermopile unit 11 and a plurality of photodiode units 12 (12-1, 12-2, 12-3, 12-4) on the same semiconductor substrate WF. Here, the photodiode unit 12-1, the photodiode unit 12-2, the photodiode unit 12-3, and the photodiode unit 12-4 have the same configuration as the above-described photodiode unit 12 and will be described as the photodiode unit 12 when indicating an arbitrary photodiode unit included in the measuring device 1*a* or not specifically distinguished.

In the present embodiment, the measuring device 1*a* differs from the above-described first embodiment in that the measuring device 1*a* includes the plurality of photodiode units 12 and the image correction unit 14.

As shown in FIG. 7, the plurality of photodiode units 12 are disposed around the thermopile unit 11 so that distances from the thermopile unit 11 are equal.

In addition, based on images detected by the plurality of the photodiode units 12, the image correction unit 14 (an example of the correction unit) generates corrected images at measurement positions of the thermopile unit 11 and outputs the generated corrected images as the images of the object. For example, the image correction unit 14 averages the color information of RGB detected by the plurality of photodiode units 12 for each primary color (each R (red), each G (green), and each B (blue)).

Since the position of the thermopile unit 11 differs from the positions of the plurality of photodiode units 12, the measurement positions of the temperature are different from the measurement positions of the images. Therefore, in the present embodiment, by averaging the color information of RGB detected by the plurality of photodiode units 12 disposed around the thermopile unit 11, the image correction unit 14 generates color information of RGB at the measurement position of the thermopile unit 11. The image correction unit 14 averages the image for each division area and corrects the image for each division area. That is, the image correction unit 14 generates a corrected image at the measurement position of the thermopile unit 11 based on the images detected by the plurality of photodiode units 12 and outputs the generated corrected image as an image of the object to the control unit 30.

In addition, since the operation of the measuring device 1*a* according to the present embodiment is the same as that of the above-described first embodiment except that the operation by the image correction unit 14 is added, the description thereof will be omitted.

As described above, the sensor unit 10*a* according to the present embodiment includes a plurality of photodiode units 12 and the image correction unit 14 (an example of the correction unit). A plurality of the photodiode units 12 (12-1, 12-2, 12-3, 12-4) are disposed around the thermopile unit 11 so that distances from the thermopile unit 11 are equal. Then, the image correction unit 14 generates a corrected image at the measurement position of the thermopile unit 11 based on the images detected by the plurality of photodiode units 12 and outputs the generated corrected image as an image of the object.

In this way, the sensor unit 10*a* according to the present embodiment may detect the image and temperature by making the detected position of the image coincide with the detected position of the temperature. Thus, since the detection positions are coincident, the sensor unit 10*a* and the measuring device 1a according to the present embodiment may analyze the characteristics of the object more accurately.

In each of the above-described embodiments, an example in which the digital mirror device 22 is applied as an example of the optical path changing unit has been described, but the present invention is not limited thereto. The optical path changing unit may be formed by combining a liquid crystal shutter and a prism, for example. That is, the optical path changing unit may include a liquid crystal shutter. In this case, the liquid crystal shutter transmits reflected light for each division area to be measured and shields reflected light from other division areas.

In addition, as another application example of the optical path changing unit, for example, a configuration including a galvano mirror, a polygon mirror, or the like may be adopted.

In addition, in the above-described second embodiment, the sensor unit 10a includes the image correction unit 14, but the control unit 30 may include the image correction unit 14.

In addition, in each of the above-described embodiments, an example in which the sensor unit 10 (10a) includes the thermopile unit 11 and the photodiode unit 12 for one pixel has been described, but the thermopile unit 11 and the photodiode unit 12 for a plurality of pixels may be included in a matrix or line form. In addition, in this case, the division area may be, for example, an area including a plurality of pixels.

In addition, in each of the above-described embodiments, an example in which the sensor unit 10 (10a) includes the thermopile unit 11 and the photodiode unit 12 formed on the same semiconductor substrate WF, but as in a multi-chip package, a configuration in which a plurality of integrated circuits are mounted on one package may be adopted. In addition, the sensor unit 10 (10a) may be configured to include a plurality of integrated circuits including a signal processing unit.

Third Embodiment

Next, the monitoring system according to the third embodiment will be described with reference to the drawing.

In the present embodiment, using the above-described measuring device 1 (1a), a monitoring system is described that monitors persons with a fever, for example at an airport, station, public facility, and the like and predicts an occurrence transition of the persons with a fever.

Figure 8:
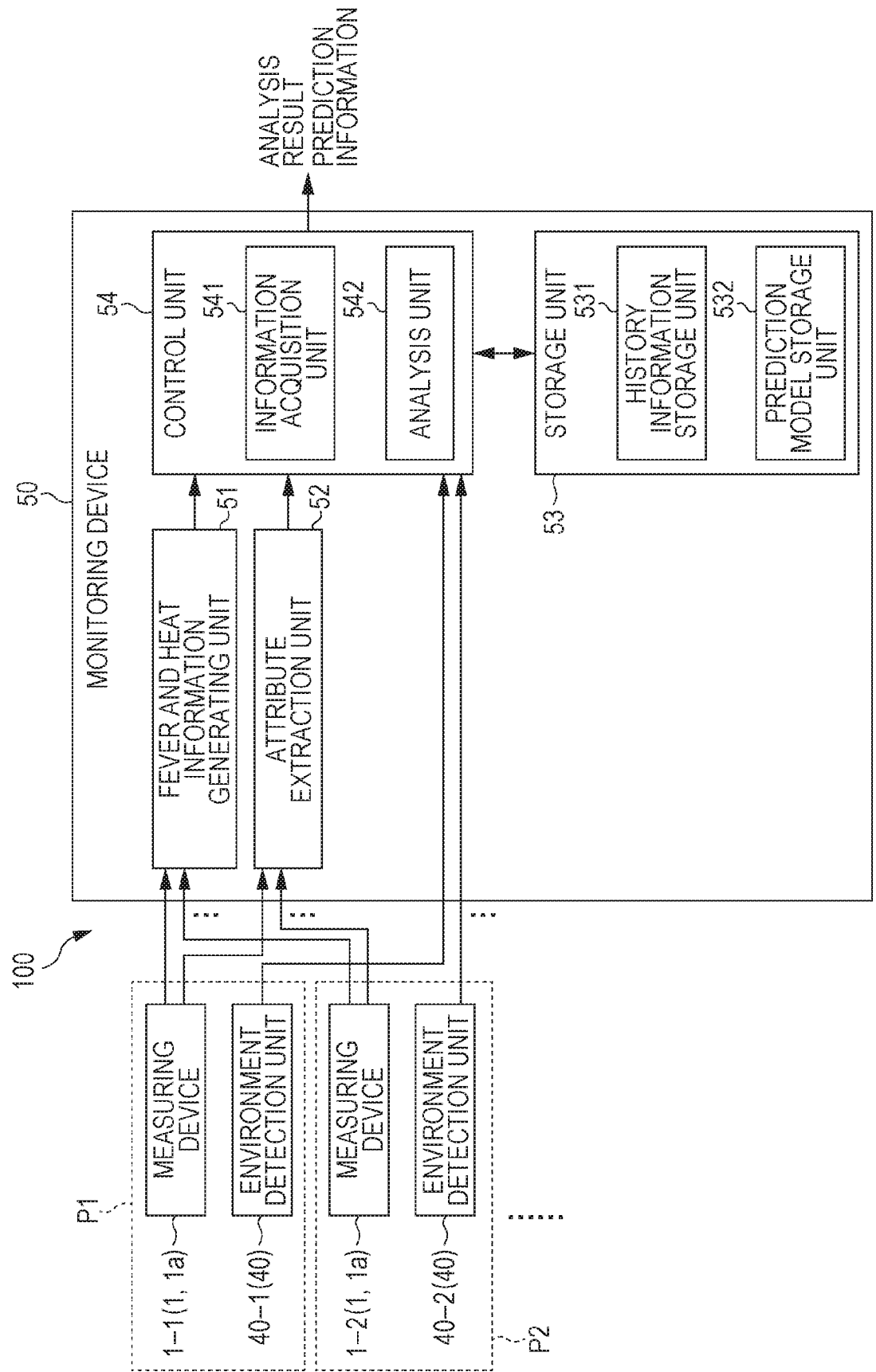
FIG. 8 is a functional block diagram showing an example of a monitoring system according to a third embodiment.

FIG. 8 is a functional block diagram showing an example of a monitoring system 100 according to the present embodiment.

As shown in FIG. 8, the monitoring system 100 includes the above-described plurality of measuring devices 1 (1a), a plurality of environment detection unit 40, and a monitoring device 50.

Either the measuring device 1 of the above-described first embodiment or the measuring device 1a of the second embodiment is applicable to the monitoring system 100, but in the present embodiment, for explanation purposes, the monitoring system 100 to which the measuring device 1 is applied will be described as follows. A measuring device 1-1, a measuring device 1-2, . . . , have the same configuration as the above-described measuring device 1 (1a) and will be described as the measuring device 1 when indicating an arbitrary measuring device included in the monitoring system 100 or not specifically distinguished.

The measuring device 1 measures the temperature distribution of at least the predetermined range (monitored area) based on infrared light and detects the image information of the predetermined range (monitored area) based on visible light.

In addition, an environment detection unit 40-1 and an environment detection unit 40-2, . . . , have the same configuration and will be described as the environment detection unit 40 when indicating an arbitrary environment detection unit included in the monitoring system 100 or not specifically distinguished.

Here, the measuring device 1-1 and the environment detection unit 40-1 are installed in a monitoring location P1 and monitor a monitored person (for example, a passerby and the like) in the monitoring location P1. In addition, the measuring device 1-2 and the environment detection unit 40-2 are installed in a monitoring location P2 and monitor a monitored person (for example, a passerby and the like) in the monitoring location P2.

The monitoring location P1 and the monitoring location P2 indicate monitored areas for monitoring the temperature of the monitored person, such as an airport, station, school, hospital, public facility, shopping mall, office, concert hall, and the like.

The environment detection unit 40 is a measuring device which detects external environment information and outputs the environment information to the monitoring device 50. The environment detection unit 40 detects the environment information indicating information on the environment of a place where the measuring device 1 is measuring, for example. Here, the environment information is, for example, a temperature, humidity, location information, and congestion degree of the monitored area. For example, the environment detection unit 40 may output the identification information (for example, name, identification ID, and the like) that identifies the monitored area as location information, and may detect accurate position coordinate information and use the position coordinate information as place information using a global positioning system (GPS) or the like. In addition, the environment detection unit 40 may detect the congestion degree of the monitored area based on the image information of a monitoring camera or the like as congestion degree.

Based on the information (for example, image information, a temperature distribution, environment information, and the like) output from the measuring device 1 (1a) and the environment detection unit 40 installed at each monitoring location, the monitoring device 50 analyzes a change in the number of persons with a fever and predicts an occurrence transition of the persons with a fever based on the analysis result. The monitoring device 50 includes, for example, a fever and heat information generating unit 51, an attribute extraction unit 52, a storage unit 53, and a control unit 54.

The fever and heat information generating unit 51 extracts a monitored person in a monitored area based on the image information of the predetermined range detected based on visible light. The fever and heat information generating unit 51 extracts the monitored person from the image information output by the measuring device 1 using existing techniques such as pattern recognition, for example. In addition, based on the temperature distribution output by the measuring device 1, the fever and heat information generating unit 51 generates fever information of the monitored person indicating a fever state corresponding to the monitored person. Here, the fever state corresponding to the monitored person is, for example, information indicating the body temperature of the monitored person extracted from the image information. In this way, the fever and heat information generating unit 51 periodically acquires the image information and the temperature distribution from the measuring device 1 and generates fever information of the monitored person based on the acquired image information and the temperature distribution. In addition, for example, the fever and heat information generating unit 51 outputs the generated fever information of the monitored person, the identification information of the monitored person, and detection time in association with each other to the control unit 54.

The identification information of the monitored person is, for example, position information of the monitored person in the image information and a sample number of the monitored person. In addition, in the above-described fever information, may be classified into a plurality of temperature ranges based on 37.0° C. or higher as a reference, for example, 37.0° C. or higher and less than 37.5° C., 37.5° C. or higher and less than 38.0° C., 38.0° C. or higher and less than 38.5° C., 38.5° C. or higher and less than 39.0° C., 39.0° C. or higher and less than 39.5° C., 39.5° C. or higher and less than 40.0° C., 40.0° C. or higher.

Based on the image information, the attribute extraction unit 52 extracts the monitored person and extracts attribute information indicating the attribute of the monitored person. The attribute information is information such as sex, age, height, and the like, for example. The attribute extraction unit 52 extracts the monitored person from the image information output by the measuring device 1 using existing techniques such as pattern recognition and extracts the attribute information of the monitored person using existing techniques such as pattern recognition. For example, the fever and heat information generating unit 51 outputs the extracted attribute information of the monitored person, the identification information of the monitored person, and detection time in association with each other to the control unit 54.

The storage unit 53 stores information used for various processes of the monitoring device 50. The storage unit 53 includes, for example, a history information storage unit 531 and a prediction model storage unit 532.

The history information storage unit 531 stores monitored person information in which at least the attribute information of the monitored person, the fever information of the monitored person, and the environment information are associated with each other for each monitored area. The monitored person information may include detection time information and the identification information of the monitored person.

The prediction model storage unit 532 stores a prediction model that is the basis of rules and determination criteria used by an analysis unit 542 of the control unit 54 to be described later to predict an occurrence transition of the persons with a fever. The prediction model is assumed to have been built in advance based on the fever information of the monitored persons in the past.

Here, a specific example of the prediction model will be described below.

As an example of the prediction model, an increase model based on a change in the number of persons whose body temperature is 38° C. or higher (number of fever patients).

Each model in increase model is defined as follows, for example.

(1) Normal state model: a model of a period during which there is no increase in the number of occurrences of fever patients or a large number of fever patients stabilize, and in a graph of the number of fever patients over time, and a case where an increase rate of the number of fever patients is within 5% in a state in which there is little difference between a linear approximation line and a polynomial approximation line.

(2) Increased occurrence state model: a model at the time when fever patients begin to increase, and in a graph of the number of fever patients over time, a case where the increase rate of the number of fever patients is 5% or more in a case where the graph may not approximate to either the linear approximation line or the polynomial approximation line.

(3) Incremental continuation model: a model at the time when fever patients are increasing, and in a graph of the number of fever patients over time, a case where the graph may more approximate to the polynomial approximation line than the linear approximation line, or there is almost no difference between the linear approximation line and the polynomial approximation line, and a case where the increase rate of the number of fever patients is more than 5%.

(4) Number of patients stabilization start model: a model at the time when a large number of fever patients begin to stabilize, and in a graph of fever patient number over time, a case where the graph may not approximate to either the linear approximation line or the polynomial approximation line and a case where the increase rate of fever patients is 5% or less.

The prediction model storage unit 532 stores definition information like the above-described increase model.

A decrease model which is a model at the time when the number of fever patients decreases can also be defined like the increase model, but the description thereof will be omitted here because, in the present embodiment, a model with an increase trend will be described.

The control unit 54 is, for example, a processor including a CPU and controls the monitoring device 50 in an integrated manner. The control unit 54 includes, for example, an information acquisition unit 541 and an analysis unit 542.

The information acquisition unit 541 (an example of the acquisition unit) acquires the fever information of the monitored person obtained based on the temperature distribution measured by the measuring device 1 in a time series. The information acquisition unit 541 periodically acquires (for a predetermined period of time) the fever information generated by the fever and heat information generating unit 51, the attribute information extracted by the attribute extraction unit 52, and the environment information detected by the environment detection unit 40. The information acquisition unit 541 causes the history information storage unit 531 to store the monitored person information in which at least the acquired fever information, attribute information, and environment information are associated with each other for each monitored area.

Based on the fever information of the monitored person acquired by the information acquisition unit 541 in a time series, the analysis unit 542 analyzes the change in the number of persons with a fever (the number of fever patients) among the monitored persons and predicts an occurrence transition of the persons with a fever based on the analysis result. The analysis unit 542 predicts an occurrence transition of the persons with a fever based on, for example, a prediction model built on the basis of the fever information of the monitored persons in the past and the change in the number of persons with a fever. That is, based on the monitored person information stored by the history information storage unit 531, the analysis unit 542 analyzes the change in the number of fever patients and predicts an occurrence transition of the persons with a fever based on the prediction model stored by the prediction model storage unit 532. For example, the analysis unit 542 determines which one of the above increase models (1) to (4) is coincident with and predicts an occurrence transition of the persons with a fever. The analysis unit 542 outputs the analyzed analysis result and the prediction information which is prediction of the occurrence transition of the persons with a fever to the outside.

A specific example in which the analysis unit 542 predicts an occurrence transition of the persons with a fever will be described later.

Next, the operation of the monitoring system 100 according to the present embodiment will be described with reference to FIG. 9.

Figure 9:
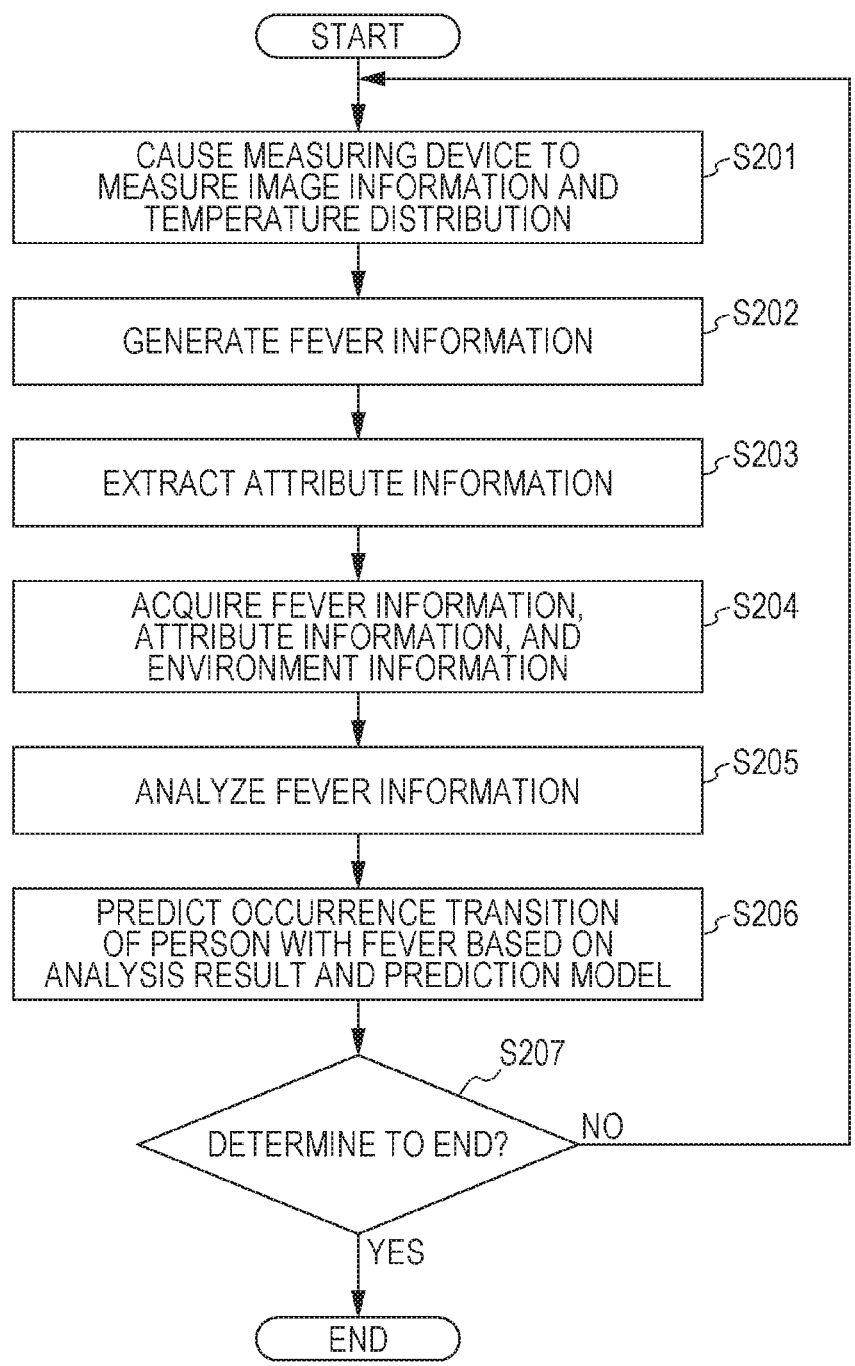
FIG. 9 is a flowchart showing an example of an operation of the monitoring system according to the third embodiment.

FIG. 9 is a flowchart showing an example of an operation of the monitoring system 100 according to the present embodiment.

In this diagram, first, the monitoring device 50 of the monitoring system 100 causes the measuring device 1 to measure image information and a temperature distribution (step S201). Each measuring device 1 measures the temperature distribution of the monitoring location (monitored area) based on infrared light and measures the image information of the monitoring location (monitored area) based on visible light.

Next, the fever and heat information generating unit 51 of the monitoring device 50 generates fever information (step S202). The fever and heat information generating unit 51 acquires the image information and the temperature distribution from the measuring device 1 and generates fever information of the monitored person based on the acquired image information and the temperature distribution. In addition, for example, the fever and heat information generating unit 51 outputs the generated fever information of the monitored person, the identification information of the monitored person, and detection time in association with each other to the control unit 54.

Next, the attribute extraction unit 52 of the monitoring device 50 extracts attribute information (step S203). Based on the image information acquired from the measuring device 1, the attribute extraction unit 52 extracts the monitored person and extracts attribute information of the monitored person. For example, the fever and heat information generating unit 51 outputs the extracted attribute information of the monitored person, the identification information of the monitored person, and detection time in association with each other to the control unit 54.

Next, the information acquisition unit 541 of the control unit 54 acquires fever information, attribute information, and the environment information (step S204). For example, the information acquisition unit 541 acquires the fever information of the monitored person generated by the fever and heat information generating unit 51, the attribute information of the monitored person extracted by the attribute extraction unit 52, and the environment information detected by the environment detection unit 40. The information acquisition unit 541 acquires the identification information of the monitored person and the detection time from the fever and heat information generating unit 51 and the attribute extraction unit 52 and associates the fever information of the monitored person and the attribute information of the monitored person to each other based on the identification information of the monitored person and the detection time. For example, the information acquisition unit 541 causes the history information storage unit 531 to store the monitored person information in which the fever information, the attribute information, the environment information are associated with each other, the identification information of the monitored person, and the detection time for each the monitored area.

Next, the analysis unit 542 of the control unit 54 analyzes fever information (step S205). Based on the monitored person's time-series monitored person information for each monitored area stored in the history information storage unit 531, the analysis unit 542 executes analysis processing for performing aggregation as shown in FIGS. 10 and 11. In addition, the analysis unit 542, for example, changes the number of persons with a fever whose body temperature is 38° C. or higher in FIG. 11 as a graph as shown in FIG. 12A to 16C and analyzes the change in the number of persons with a fever by generating the linear approximation line and the polynomial approximation line.

Next, the analysis unit 542 predicts an occurrence transition of the persons with a fever based on the analysis result and the prediction model (step S206). For example, based on graphs shown in FIGS. 12A to 16C which will be described later, which are analysis results, and the prediction model stored by the prediction model storage unit 532, the analysis unit 542 predicts an occurrence transition of the persons with a fever. For example, the analysis unit 542 determines which one of the above increase models (1) to (4) is coincident with and predicts an occurrence transition of the persons with a fever.

Next, the control unit 54 determines whether or not to end the operation of the monitoring device 50 (step S207). In a case where the control unit 54 ends the operation (step S207: YES), the control unit 54 ends the operation. In addition, in a case where the operation does not end (operation continues) (step S207: NO), the control unit 54 returns the processing to step S201 and repeats the processing from step S201 to step S207.

In this way, in the monitoring device 50, the analysis unit 542 periodically analyzes and predicts an occurrence transition of the persons with a fever.

The analysis unit 542 may output (notify) information indicating that an abnormality has occurred, in addition to predicting an occurrence transition, in a case where an abnormality such as a rapid increase of persons with a fever occurs. That is, the analysis unit 542 determines that an abnormality occurs, for example, in a case where the number of fever patients whose body temperature is 38° C. or higher exceeds a predetermined number within a predetermined unit time, and may display a message indicating that an abnormality has occurred on a display unit (not shown), for example and output an alarm by sound, buzzer, or the like.

Next, a specific example of the processing of the analysis unit 542 will be described with reference to FIGS. 10 to 16C.

FIGS. 10 and 11 are diagrams showing an example of analysis results of the monitoring system 100 according to the present embodiment.

The example shown in FIG. 10 is a result of aggregating, for example, the body temperature of the monitored person in a measurement target area every 10 minutes from the time "10:00" on a certain day by the analysis unit 542 based on the monitored person information stored by the history information storage unit 531.

In addition, the example shown in FIG. 11 shows an analysis result of aggregating the number of monitored persons per body temperature and the increase rate (%) of the persons whose body temperature is 38° C. or higher, for example, in a population of 100 monitored persons by the analysis unit 542 based on the aggregation result shown in FIG. 10.

In the example shown in FIG. 11, the analysis unit 542 classifies "body temperature (° C.)" as "35 to 36" (35° C. or higher and less than 36° C.), "36 to 37" (36° C. or higher and less than 37° C.), "37 to 38" (37° C. or higher and less than 38° C.), and "38 or higher" (38° C. or higher) at each time and aggregates the number of persons thereof. In addition, the analysis unit 542 calculates the increase rate of the number of monitored persons classified as "38 or higher" (38° C. or higher) at each time and aggregates the increase rate as "increase rate (%)."

In the example shown in FIG. 11, at the time "10:30", the number of persons whose body temperature is "38 or higher" (38° C. or higher) is "43" (43 persons), and "increase rate (%)" is "42" (42%). In addition, at the time "10:40", the number of persons whose body temperature is "38 or higher" (38° C. or higher) is "62" (62 persons), and "increase rate (%)" is "19" (19%). In the present embodiment, the increase rate shows the ratio of how many people have increased from a previous measurement time in the population of 100 persons.

Next, the prediction of the occurrence transitions of persons with a fever by the analysis unit 542 will be described with reference to FIGS. 12A to 16C.

FIGS. 12A to 16C are diagrams showing examples of state determination by the increase model in the present embodiment.

Each of the diagrams of FIGS. 12A to 16C is a result of a graph (graph of the number of fever patients over time) drawn by the analysis unit 542 every 10 minutes from the time "10:20" to the time "11:00" based on the analysis result shown in FIG. 11. In addition, FIGS. 12A, 13A, 14A, 15A, and 16A show changes (hereinafter, referred to as a change in the number of fever patients at a target time over time) in the number of persons whose body temperature is 38° C. or higher two times in the past and the number of persons whose body temperature is 38° C. or higher at a target time in graphs. In addition, FIGS. 12B, 13B, 14B, 15B, and 16B show changes in the number of fever patients at the target time over time and a comparison with the linear approximation line, and FIGS. 12C, 13C, 14C, 15C, and 16C show changes in the number of fever patients at the target time and a comparison with the polynomial approximation line.

In the graphs of FIGS. 12A to 16C, the vertical axis shows the number of fever patients and the horizontal axis shows time.

Figure 12A:
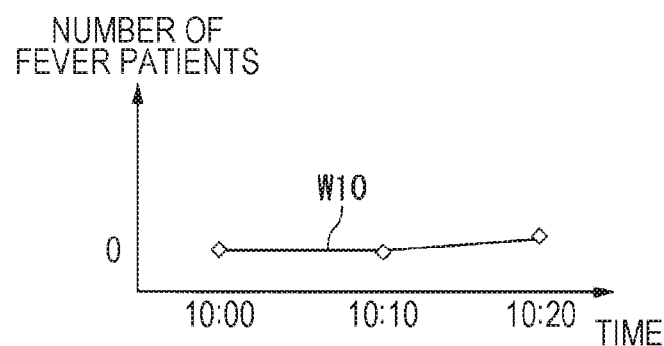
FIG. 12A is a first diagram showing an example of state determination by an increase model in the third embodiment.
Figure 12B:
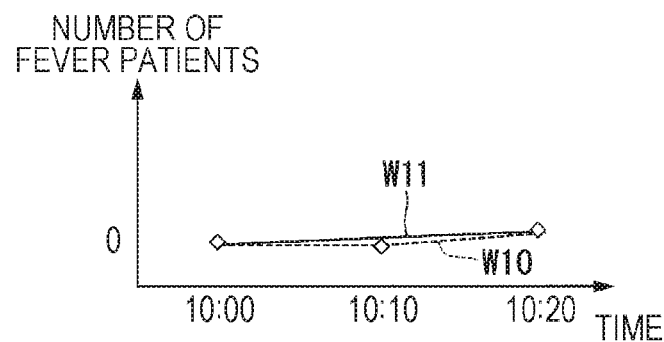
FIG. 12B is a second diagram showing an example of state determination by the increase model in the third embodiment.
Figure 12C:
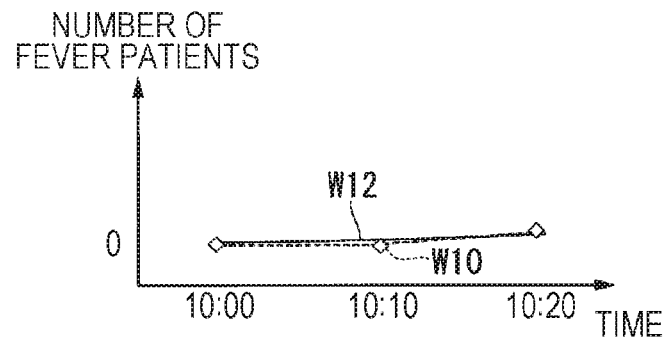
FIG. 12C is a third diagram showing an example of state determination by the increase model in the third embodiment.

The examples shown in FIGS. 12A, 12B, and 12C show graphs at time "10:20", a waveform W10 shows the number of fever patients at time "10:20" over time, a waveform W11 shows the linear approximation line, and a waveform W12 shows the polynomial approximation line. In the example shown in FIGS. 12A, 12B, and 12C, in the graphs of the number of fever patients over time, since there is little difference between the linear approximation line and the polynomial approximation line and the increase rate of fever patients is within 5%, the analysis unit 542 determines that the state is the "normal state model".

Figure 13A:
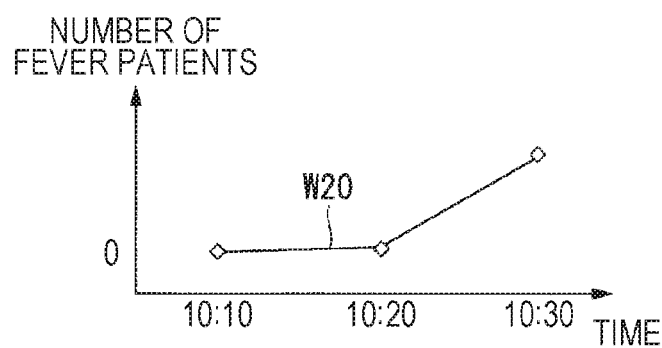
FIG. 13A is a fourth diagram showing an example of state determination by the increase model in the third embodiment.
Figure 13B:
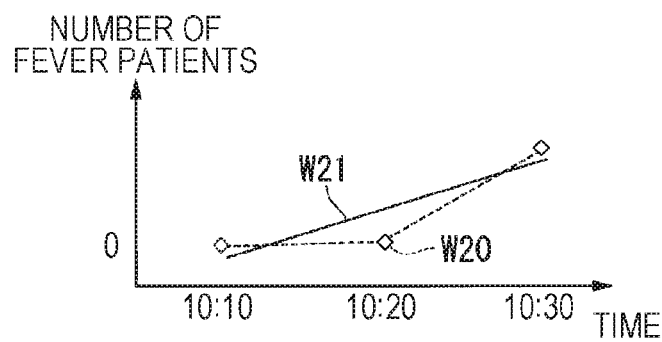
FIG. 13B is a fifth diagram showing an example of state determination by the increase model in the third embodiment.
Figure 13C:
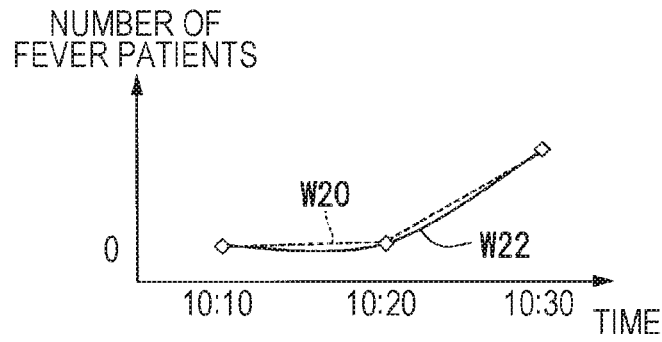
FIG. 13C is a sixth diagram showing an example of state determination by the increase model in the third embodiment.

In addition, the examples shown in FIGS. 13A, 13B, and 13C show graphs at a time "10:30", a waveform W20 shows the number of fever patients at a time "10:30" over time, a waveform W21 shows the linear approximation line, and a waveform W22 shows the polynomial approximation line. In the examples shown in FIGS. 13A, 13B, and 13C, since the graphs may not approximate to either the linear approximation line or the polynomial approximation line, and the increase rate of the number of fever patients is 5% or more, the analysis unit 542 determines that the state is the "increased occurrence model".

Figure 14A:
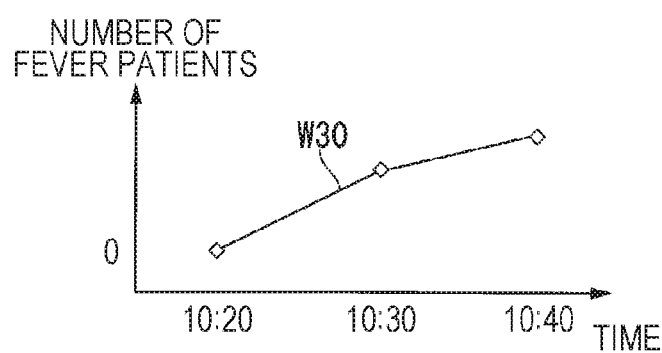
FIG. 14A is a seventh diagram showing an example of state determination by the increase model in the third embodiment.
Figure 14B:
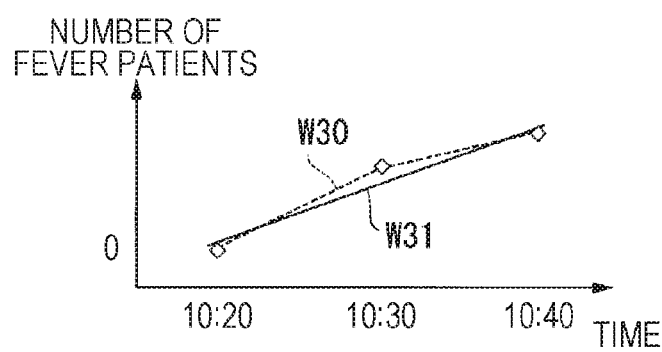
FIG. 14B is an eighth diagram showing an example of state determination by the increase model in the third embodiment.
Figure 14C:
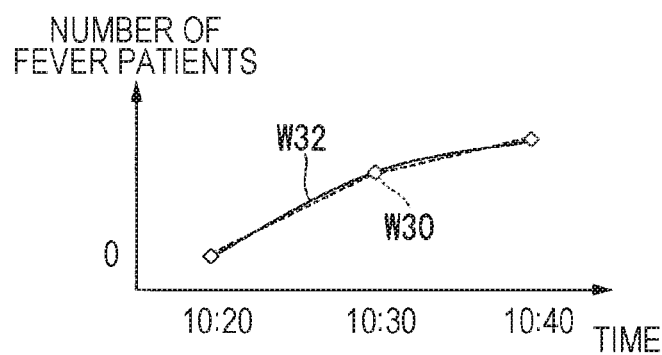
FIG. 14C is a ninth diagram showing an example of state determination by the increase model in the third embodiment.

In addition, the examples shown in FIGS. 14A, 14B, and 14C show graphs at a time "10:40", a waveform W30 shows the number of fever patients at a time "10:40" over time, a waveform W31 shows the linear approximation line, and a waveform W32 shows the polynomial approximation line. In the example shown in FIGS. 14A, 14B, and 14C, in a case where the graphs may more approximate to the polynomial approximation line than the linear approximation line, since the increase rate of the number of fever patients is more than 5%, the analysis unit 542 determines that the state is the "incremental continuation model".

Figure 15A:
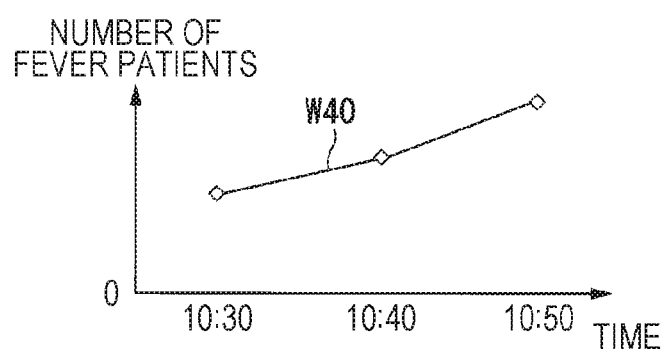
FIG. 15A is a tenth diagram showing an example of state determination by the increase model in the third embodiment.
Figure 15B:
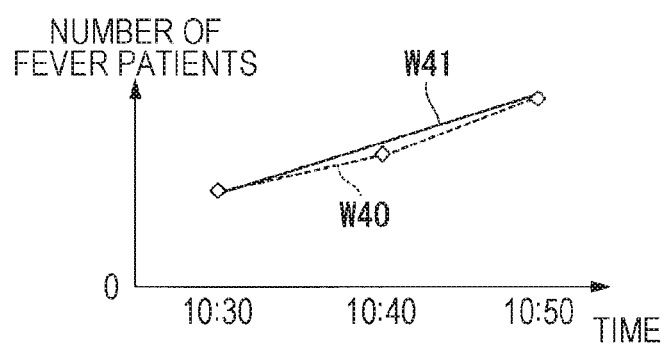
FIG. 15B is an eleventh diagram showing an example of state determination by the increase model in the third embodiment.
Figure 15C:
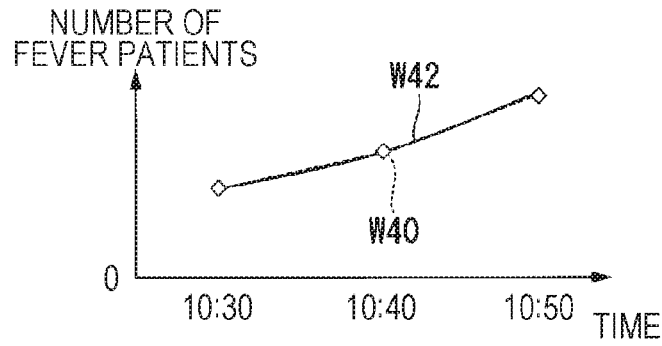
FIG. 15C is a twelfth diagram showing an example of state determination by the increase model in the third embodiment.

In addition, the examples shown in FIGS. 15A, 15B, and 15C show graphs at time "10:50", a waveform W40 shows the number of fever patients at time "10:50" over time, a waveform W41 shows the linear approximation line, and a waveform W42 shows the polynomial approximation line. In the example shown in FIGS. 15A, 15B, and 15C, in a case where the graphs may more approximate to the polynomial approximation line than the linear approximation line, since the increase rate of the number of fever patients is more than 5%, the analysis unit 542 determines that the state is the "incremental continuation model".

Figure 16A:
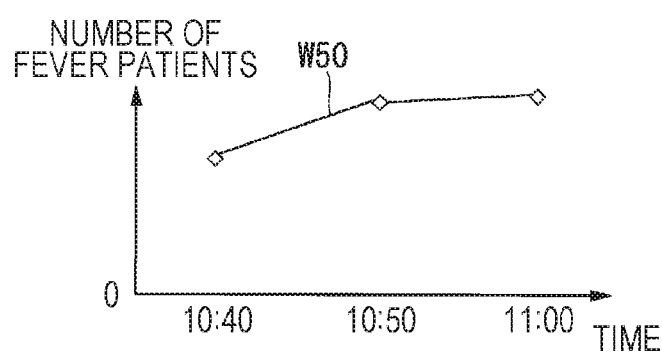
FIG. 16A is a thirteenth diagram showing an example of state determination by the increase model in the third embodiment.
Figure 16B:
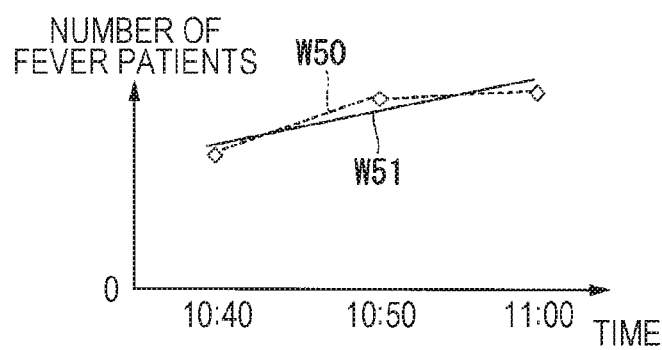
FIG. 16B is a fourteenth diagram showing an example of state determination by the increase model in the third embodiment.
Figure 16C:
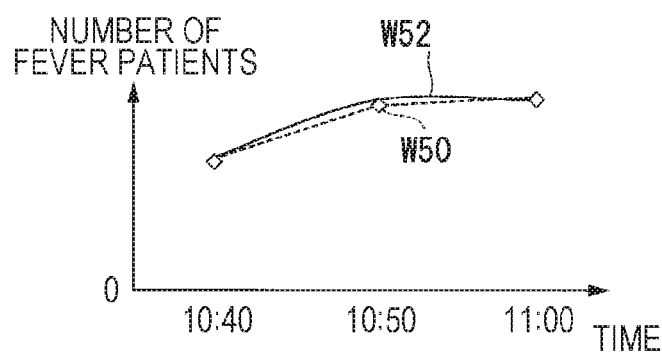
FIG. 16C is a fifteenth diagram showing an example of state determination by the increase model in the third embodiment.

In addition, the examples shown in FIGS. 16A, 16B, and 16C show graphs at a time "11:00", a waveform W50 shows the number of fever patients at a time "11:00" over time, a waveform W51 shows the linear approximation line, and a waveform W52 shows the polynomial approximation line. In the examples shown in FIGS. 16A, 16B, and 16C, since the graphs may not approximate to either the linear approximation line or the polynomial approximation line, and the increase rate of the number of fever patients is less than 5%, the analysis unit 542 determines that the state is the "number of patients stabilization start model".

In this way, in the monitoring device 50, the analysis unit 542 compares a graph of the change of the number of fever patients over time, which is an analysis result, with each prediction model, thereby determining what kind of state the occurrence of a fever patient is.

In the above-described example, an example in which the analysis unit 542 uses fever information only has been described, but by adding attribute information or environment information, it is possible to make changes to the determination of the state of occurrence. For example, the analysis unit 542 may estimate (predict) that the number of fever patient is in an early stage of occurrence in a case where it is analyzed that a fever situation is distributed in many young people based on the attribute information. In addition, for example, even though there is a lot of fever in some of the monitoring locations, in a case where there is a little fever in the monitoring location where relatively young people gathers, the analysis unit 542 may estimate (predict) that the number of fever patients is not increasing.

In addition, for example, the analysis unit 542 may estimate (predict) an increase rate of infection by determining the activity status of virus (for example, influenza, and the like) from temperature and humidity which are the environment information. For example, if conditions that increase the risk of catching a disease are set in advance, such as seasons and a case where temperature and humidity are low, the analysis unit 542 may be utilized to create a better prediction model.

Generally, in the case of influenza, in a case where an air temperature is 10° C. or less, and relative humidity is 50% or less (for example, 15% to 40%) at room temperature, the lower the inactivation rate of the virus, and the more days the average relative humidity is 50% or less, the more the infection is to occur. In addition, the more days the average relative humidity is 60% or higher, the infection passes lightly, and the analysis unit 542 may create a prediction model with higher accuracy by including environment information.

In this way, by adding rules that are empirically derived from the past occurrence situations to the prediction model, the monitoring device 50 may increase the accuracy in predicting an occurrence transition of the persons with a fever.

As explained above, the monitoring system 100 according to the present embodiment is a system including the measuring device 1 and the monitoring device 50 that measure the temperature distribution of at least the predetermined range (for example, a monitored area) based on infrared light. The monitoring device 50 includes the information acquisition unit 541 (an example of the acquisition unit) and the analysis unit 542. The information acquisition unit 541 acquires fever information of the monitored person indicating the fever state corresponding to the monitored person extracted based on the image information of the predetermined range detected on the basis of visible light, and fever information of the monitored person obtained on the basis of the temperature distribution measured by the measuring device 1 in a time series. The analysis unit 542 analyzes the change in the number of persons with a fever among the monitored persons based on the fever information of the monitored persons acquired by the information acquisition unit 541 in a time series and predicts an occurrence transition of the persons with a fever based on the analysis result.

In this way, the monitoring system 100 and the monitoring device 50 according to the present embodiment analyze the change in the number of persons with a fever and predicts an occurrence transition of the persons with a fever so that the monitoring person is able to grasp the situation of a person with a fever more efficiently and takes countermeasures.

In addition, for example, a case is considered, where the monitoring device 50 is installed in a public facility, an airport, a station, a school, a hospital, a shopping mall, an office, a concert hall, and the like. In this case, for example, by building big data connected to a high-speed network and storing the occurrence situation of the fever patients in a database in each monitoring device 50, in the monitoring system 100 and the monitoring device 50 according to the present embodiment, it is possible to identify fever patients in a real-time. In addition, in the monitoring system 100 and the monitoring device 50 according to the present embodiment, it is possible for a monitoring person to grasp the situation more efficiently and take countermeasures, such monitoring the occurrence situation of a pandemic, calling attention, and the like.

In addition, in the present embodiment, the monitoring system 100 includes the attribute extraction unit 52 that extracts the monitored person based on image information and extracts attribute information indicating the attribute of the monitored person. The analysis unit 542 predicts an occurrence transition of the persons with a fever based on the fever information of the monitored persons and the attribute information extracted by the attribute extraction unit 52.

In this way, the monitoring system 100 according to the present embodiment may create a more accurate prediction model by adding the attribute information. Therefore, the monitoring system 100 and the monitoring device 50 according to the present embodiment may increase the accuracy in predicting an occurrence transition of the persons with a fever.

In addition, in the present embodiment, the monitoring system 100 includes the environment detection unit 40 that detects environment information indicating information on the environment of a place where the measuring device 1 is measuring. The analysis unit 542 predicts an occurrence transition of the persons with a fever based on the fever information of the monitored persons and the environment information detected by the environment detection unit 40.

In this way, the monitoring system 100 according to the present embodiment may create a more accurate prediction model by adding the environment information. Therefore, the monitoring system 100 and the monitoring device 50 according to the present embodiment may increase the accuracy in predicting an occurrence transition of the persons with a fever.

In addition, in the present embodiment, the measuring device 1 includes the sensor unit 10 having the thermopile unit 11 that detects the temperature of the object based on the infrared light reflected from the object, and the photodiode unit 12 that detects the image of the object based on the visible light reflected from the object, on the same substrate, and measures the temperature distribution and measures the image information.

In this way, since the measuring device 1 may detect the image of the object along with the temperature of the object, in the monitoring system 100 according to the present embodiment, it possible to accurately analyze the characteristics of a monitored target person together with the body temperature of the monitored target person. Therefore, in the monitoring system 100 according to the present embodiment, it is possible for the monitoring person to grasp the situation of a person with a fever more efficiently and take countermeasures.

In addition, in the present embodiment, the analysis unit 542 predicts an occurrence transition of persons with a fever based on the prediction model built based on the fever information of the monitored persons in the past and the change in the number of persons with a fever.

In this way, the monitoring system 100 and the monitoring device 50 according to the present embodiment may accurately predict an occurrence transition of persons with a fever by the simple method using the prediction model.

In addition, the monitoring method according to the present embodiment includes a measurement step, an acquisition step, and an analysis step. In the measurement step, the measuring device 1 measures the temperature distribution of at least the predetermined range based on infrared light. In the acquisition step, the monitoring device 50 acquires fever information of the monitored person indicating the fever state corresponding to the monitored person extracted based on the image information of the predetermined range detected on the basis of visible light, and fever information of the monitored person obtained on the basis of the temperature distribution measured by the measurement step in a time series. In the analysis step, based on the fever information of the monitored person acquired in a time series in the acquisition step, the monitoring device 50 analyzes the change in the number of persons with a fever among the monitored persons and predicts an occurrence transition of the persons with a fever based on the analysis result.

In this way, the monitoring method according to the present embodiment analyzes the change in the number of persons with a fever and predicts an occurrence transition of the persons with a fever so that the monitoring person is able to grasp the situation of a person with a fever more efficiently and takes countermeasures.

In the above-described embodiment, an example in which the monitoring device 50 includes the fever and heat information generating unit 51 and the attribute extraction unit 52 has been described, but the present invention is not limited thereto. The monitoring device 50 may have one or both of the fever and heat information generating unit 51 and the attribute extraction unit 52. In addition, the control unit 54 may include one or both of the fever and heat information generating unit 51 and the attribute extraction unit 52.

In addition, in the above-described embodiment, an example in which the monitoring system 100 includes the environment detection unit 40 has been described, but the monitoring system 100 may not include the environment detection unit 40.

In addition, in the above-described embodiment, an example in which the measuring device 1 and the environment detection unit 40 are directly connected to the monitoring device 50 has been described, but the measuring device 1 and the environment detection unit 40 may be connected to the monitoring device 50 via a network. In addition, the measuring device 1 and the environment detection unit 40 may store the measurement information in a server device on a network, and the monitoring device 50 may acquire the measurement information from the server device.

In addition, in the above-described embodiment, an example in which the prediction model is built in advance has been described, but the analysis unit 542 may build the prediction model based on the past measurement information. In addition, in this case, the analysis unit 542 may periodically rebuild (update) the prediction model. By periodically rebuilding (updating) the prediction model, the monitoring system 100 may improve prediction accuracy.

In addition, in the above embodiment, an example in which the monitoring system 100 measures with the measuring device 1 according to the first embodiment an example has been described, but the present invention is not limited thereto. For example, the monitoring system 100 may be the measuring device 1a according to the second embodiment or may be configured such that different devices measure temperature distribution and image information.

The present invention is not limited to each of the above-described embodiments and may be modified within a range not departing from the gist of the present invention.

The above-described monitoring system 100 includes a computer system therein. Then, processing in each configuration of the above-described monitoring system 100 may be performed by recording a program for realizing the functions of each configuration of the above-described monitoring system 100 on a computer-readable recording medium, causing a computer system to read the program recorded on the recording medium and execute the program. The "computer system" referred to here is a computer system built in the monitoring system 100 and includes hardware such as an OS and peripheral devices. In addition, the "computer-readable recording medium" refers to a storage medium such as a flexible disk, a magneto-optical disk, a portable medium such as a ROM or a CD-ROM, or a hard disk built in the computer system. Furthermore, the "computer-readable recording medium" may include a medium that dynamically holds a program for a short period of time, such as a communication line in the case of transmitting a program via a network such as the Internet or a communication line such as a telephone line, and a medium that holds a program for a certain period of time, such as a volatile memory inside a computer system serving as a server or a client in that case. Further, the above-described program may be a program for realizing a part of the above-described functions, or may be realized by combining the above-mentioned function with a program already recorded in the computer system.

In addition, some or all of the above-described functions may be realized as an integrated circuit of large scale integration (LSI) or the like. Each of the above-described functions may be individually realized as a processor, or a part or the whole thereof may be integrated into a processor. In addition, the integrated circuit method is not limited to LSI, but may be realized by a dedicated circuit or a general-purpose processor. In addition, in a case where a technique of replacing the LSI emerges as a result of advances in semiconductor technology, the integrated circuit by the technique may be used.

The present invention may also be implemented in the following aspect.

(1) An integrated circuit including, on a same substrate, a first detection element that detects a temperature of an object based on infrared light reflected from the object and a second detection element that detects an image of the object based on visible light reflected from the object.

(2) The integrated circuit according to (1) in which the first detection element detects the temperature of the object based on the infrared light and reflectance of the object generated based on the image detected by the second detection element.

(3) The integrated circuit according to (2) in which the reflectance of the object is generated based on a color and a brightness of the object based on the image detected by the second detection element.

(4) The integrated circuit according to any one of (1) to (3) further including a plurality of second detection elements disposed around the first detection element so that distances from the first detection element are equal to each other and a correction unit that generates corrected images at measurement positions of the first detection element based on images detected by the plurality of second detection elements and outputs the generated corrected images as images of the object.

(5) A measuring device including the integrated circuit according to any one of (1) to (4), an optical path changing unit that is capable of changing optical paths of infrared light and visible light incident from each of division areas into which a predetermined detection range is divided and emitting the infrared light and the visible light toward the first detection element and the second detection element, and a measurement control unit that causes the optical path changing unit to emit, to the integrated circuit, the infrared light and the visible light incident from each of the division areas into which the predetermined detection range is divided while changing the division areas and causes the integrated circuit to detect a temperature and an image for each of the division areas.

(6) The measuring device according to (5) further including an output processing unit that generates the images of the predetermined detection range based on the image of the object and the temperature of the object in each of the division areas detected by the integrated circuit and outputs the images of the predetermined detection range and the temperature of the object in each of the division areas in association with each other.

REFERENCE SIGNS LIST 1, 1a, 1-1, 1-2 measuring device
10, 10a sensor unit 11 thermopile unit
12, 12-1, 12-2, 12-3, 12-4 photodiode unit
12R red photodiode unit
12G green photodiode unit
12B blue photodiode unit
13 transistor
14 image correction unit
20 optical system
21, 23 lens
22 digital mirror device
30, 54 control unit
31 measurement control unit
32 reflectance generating unit
33 output processing unit
40, 40-1, 40-2 environment detection unit
50 monitoring device
51 fever and heat information generating unit
52 attribute extraction unit
53 storage unit
100 monitoring system
111 thermopile
112 cavity
113 heat sink portion
121 microlens
122 color filter
123 light shielding film
124 photodiode
125 polysilicon
131 source portion
132 drain portion
133 gate portion
531 history information storage unit
532 prediction model storage unit
541 information acquisition unit
542 analysis unit
P1, P2 monitoring location
WF semiconductor substrate

The invention claimed is:

1. An integrated circuit comprising: first detection circuitry that detects a temperature of an object based on infrared light reflected from the object, the first detection circuitry being on a first position of a substrate; second detection circuitry that detects a first image of the object based on first visible light reflected front the object, the second detection circuitry being on a second position of the substrate, the second position being different from the first position, a first distance from the first detection circuitry to the second detection circuitry being a predetermined distance; third detection circuitry that detects a second image of the object based on second visible light reflected from the object, the third detection circuitry being on a third position of the substrate, the third position being different from the first position, a second distance from the first detection circuitry to the third detection circuitry being the predetermined distance; and correction circuitry that; generates a corrected image at a measurement position of the first detection circuitry based on the first and second images detected by the second and third detection circuitries, and without using a third image at the measurement position of the first detection circuitry, and outputs the generated corrected image, the corrected image including color information of red, green, and blue.

2. The integrated circuit according to claim 1,
wherein the first detection circuitry detects the temperature based on the infrared light, a first reflectance of the object generated based on the first image detected by the second detection circuitry, and a second reflectance of the object generated based on the second image detected by the third detection circuitry.

3. The integrated circuit according to claim 2,
wherein the first reflectance and the second reflectance are generated based on a color and a brightness of the object based on the first and second images detected by the second and third detection circuitries.

4. A measuring device comprising:
the integrated circuit according to claim 1;
optical path changing circuitry that changes optical paths of infrared light and visible light incident from each of division areas into which a predetermined detection range is divided and emits the infrared light and the visible light toward the first, second, and third detection circuitries; and
measurement control circuitry that causes the optical path changing circuitry to emit, to the integrated circuit, the infrared light and the visible light incident from each of the division areas into which the predetermined detection range is divided while changing the division areas and causes the integrated circuit to detect a temperature and an image for each of the division areas.

5. The measuring device according to claim 4, the measuring device further comprising
output processing circuitry that generates an image of the predetermined detection range based on the image of the object and the temperature of the object in each of the division areas detected by the integrated circuit and outputs the images of the predetermined detection range and the temperature of the object in each of the division areas in association with each other.

6. The integrated circuit according to claim 1,
wherein a straight line connecting the second detection circuitry and the third detection circuitry passes through the first detection circuitry.

7. The integrated circuit according to claim 1, the integrated circuit further comprising:
fourth detection circuitry that detects a third image of the object based on third visible light reflected from the object, the fourth detection circuitry being on the substrate, a third distance from the first detection circuitry to the fourth detection circuitry being the predetermined distance; and
fifth detection circuitry that detects a fourth image of the object based on fourth visible light reflected from the object, the fifth detection circuitry being on the substrate, a fourth distance from the first detection circuitry to the fifth detection circuitry being the predetermined distance, wherein
the first detection circuitry is disposed at a center of a quadrangle on the substrate, the quadrangle having first to fourth corners,
the second detection circuitry is disposed at the first corner,
the third detection circuitry is disposed at the second corner,
the fourth detection circuitry is disposed at the third corner,
the fifth detection circuitry is disposed at the fourth corner, and
the correction circuitry generates the corrected image based on the third and fourth images detected by the fourth and fifth detection circuitries in addition to the first and second images detected by the second and third detection circuitries.

8. The integrated circuit according to claim 1,
wherein the correction circuitry generates the corrected image by averaging first color information of the first image detected by the second detection circuitry and second color information of the second image detected by the third detection circuitry.

9. The integrated circuit according to claim 1, wherein:
the first detection circuitry does not detect an image of the object, and
the second detection circuitry and the third detection circuitry do not detect the temperature of the object.

10. The integrated circuit according to claim 1, further comprising:
an output processor that simultaneously outputs the temperature detected by the first detection circuitry and the corrected image generated by the correction circuitry.

* * * * *